US008642317B2

(12) United States Patent
Zhou et al.

(10) Patent No.: US 8,642,317 B2
(45) Date of Patent: Feb. 4, 2014

(54) BACTERIAL ISOLATE AND METHODS FOR DETOXIFICATION OF TRICHOTHECENE MYCOTOXINS

(75) Inventors: Ting Zhou, Guelph (CA); Jianhua Gong, Guelph (CA); Hai Yu, Guelph (CA); Xiu-Zhen Li, Guelph (CA)

(73) Assignee: Her Majesty the Queen in right of Canada, as represented by the Minister of Agriculture and Agri-Food, Ontario (CA)

( * ) Notice: Subject to any disclaimer, the term of this patent is extended or adjusted under 35 U.S.C. 154(b) by 600 days.

(21) Appl. No.: 12/671,514

(22) PCT Filed: Jul. 31, 2008

(86) PCT No.: PCT/CA2008/001402

§ 371 (c)(1),
(2), (4) Date: Jun. 7, 2010

(87) PCT Pub. No.: WO2009/015478

PCT Pub. Date: Feb. 5, 2009

(65) Prior Publication Data

US 2010/0239537 A1 Sep. 23, 2010

Related U.S. Application Data

(60) Provisional application No. 60/953,301, filed on Aug. 1, 2007.

(51) Int. Cl.
*C12N 1/20* (2006.01)

(52) U.S. Cl.
USPC ........................ 435/252.5; 426/61; 424/93.46

(58) Field of Classification Search
None
See application file for complete search history.

(56) References Cited

U.S. PATENT DOCUMENTS 7,347,997 B1 * 3/2008 Binder et al. ................ 424/93.1

FOREIGN PATENT DOCUMENTS

CA 2317065 A1 7/1999

OTHER PUBLICATIONS

Shima et al., Applied and Environmental Microbiology, Oct. 1997, p. 3825-3830 vol. 63, No. 10.*
Young, J.C., et al. "Degradation of Trichothecene Mycotoxins by Chicken Intestinal Microbes." Food and Chemical Toxicology, 45: 136-143 (Jan. 2007) ISSN: 0278-6915.
Zhou, T., et al. "Microbial Transformation of the Trichothecene Mycotoxins." World Mycotoxin Journal, 1(1): 23-30 (Feb. 2008) ISSN: 1875-0710.
Shima, J. et al. "Novel Detoxification of the Trichothecene Mycotoxin Deoxynivalenol by a Soil Bacterium Isolated by Enrichment Culture." Applied and Environmental Microbiology, 63(10): 3825-3830 (Oct. 1997) ISSN: 0099-2240.
PCT/ISA/210—ISR issued in PCT/CA2008/001402, Oct. 23, 2008, Her Majesty the Queen in Right of Canada, etc.
PCT/ISA/237—Written Opinion issued in PCT/CA2008/001402, Oct. 23, 2008, Her Majesty the Queen in Right of Canada, etc.
Li, X.Z., Zhu, C.H., de Lange, C. F.M., Zhou, T., He, J., Yu, H., Gong, J., Zhu, H., and Young, J.C. (2008). Demonstration of deoxynivalenol (DON) detoxification by a bacterial isolate in a swine feeding trial. The fifth conference of the World Mycotoxin Forum, Noordwijk, the Netherlands, Nov. 17-18, 2008. p. 142.
Li, X.Z., Zhu, C.H., de Lange, C. F.M., Zhou, T., He, J., Yu, H., Gong, J., Zhu, H., and Young, J. C. (2008). Microbial detoxification of deoxynivalenol (DON) demonstrated in a swine feeding trial. The 2008 Canadian Institute of Food Science & Technology (CIFST/AAFC) Conference, Charlottetown, PEI, May 25-27, 2008.
Zhou, T. (2008). Microbial Detoxification of Trichothecene Mycotoxins. The 2008 Canadian Institute of Food Science & Technology (CIFST/AAFC) Conference, Charlottetown, PEI, May 25-27, 2008.
Young J.C, T. Zhou, H.Yu,H. Zhu, J. Gong. 2007. Degradation of trichothecene mycotoxins by chichen intestinal microbes. Food and Chemical Toxicology 45(2007) 136-143.
Islam, M.R., Pauls, K.P. and Zhou, T. (2008). Isolation and characterization of soil bacteria capable of detoxifying mycotoxin dexinivalenol. Phytopathology 98:S72.
Yu, H., Zhou, T., Gong, J., Young, J.C., Li, X.Z., Zhu, H., Tsao, R., and Yang, R. (2008). Isolation and characterization of chicken gut bacterial capable of detoxifying vomitoxin (deoxynivalenol). The 2008 Canadian Institute of Food Science & Technology (CIFST/AAFC) Conference, Charlottetown, PEI, May 25-27, 2008.
Zhou, T., Gong, J., Young, J.C., Yu, H., Li, X.-Z., Zhu, H., Hill, A., Yang, R., de Lange, C.F.M., Du, W., and Tsao, R. 2007. "Microorganisms Isolated from Chicken Gut Can Effectively Detoxify DON and Other Trichothecene Mycotoxins.", 26th Annual Centralia Swine Research Update, Kirkton-Woodham Community Centre, Kirkton, ON, Canada, Jan. 31, 2007, pp. II-33-II-34.
Gong, J., Zhou, T., Young, J.C., Cottrill, M., Yu, H., Zhu, H., de Lange, C.F.M., Du, W. and Cao, R. 2003. Gut microbes and mycotoxin: Can chicken gut microbes detoxify vomitoxin? Proceeding of the 22nd Annual Centralia Swine Research Update, Kirkton, Ontario. pp. I 30-I 31.
Zhou, T., Gong, J., Young, J.C., Yu, H., Zhu, H., Su, X.J., Li, X.Z., Yang, R., de Lange, C.F.M., Du, W., and Cao, R. 2005. Detoxification of vomitoxin with bio-transforming microorganisms. 24th Annual Centralia Swine Research Update, Jan. 6, Kirkton, Ontario, Canada.
Gong, J. and Zhou, T. 2007. Isolation of gut bacteria capable of detoxifying trichothecene mycotoxins. Proceeding of the 7th International Conference of Food Science and Technology (Nov. 12-16), Wuxi, Jiangsu, China.
Gong, J., Zhou, T., Yu, H., Young, J.C., Zhu, H., Su, X.J., Li, X.Z., Yang, R., de Lange, C.F.M., Du, W., and Cao, R. 2006. Detoxification of mycotoxins: a microbiological approach. The World Mycotoxin Forum—the 4th Conference, Nov. 6-8, Cincinnati, Ohio, USA. pp. 70-71.

(Continued)

*Primary Examiner* — Irene Marx

(74) *Attorney, Agent, or Firm* — Saul Ewing LLP; Peter C. Lauro, Esq.

(57) ABSTRACT

The invention provides a bacterial isolate defined by accession number 180507-1 filed with the International Depository Authority of Canada. The bacteria are capable of degrading trichothecene mycotoxins. Also provided are compositions comprising the bacteria and methods of preventing or treating food, foodstuffs, crops and harvested crops that are contaminated or susceptible to contamination with trichothecene mycotoxins. Kits are also provided.

1 Claim, 6 Drawing Sheets

(56) References Cited

OTHER PUBLICATIONS

He, J., et al., Sample clean-up methods, immunoaffinity chromatography and solid phase extraction, for determination of deoxynivalenol and deepoxy doxynivalenol in swine serum, Mycotox Res (2009) 25:89-94.

He, J., et al., Chemical and biological transformations for detoxification of trichothecene mycotoxins in human and animal food chains: a review, Trends in Food Science & Technology 21 (2010) 67-76.

Li, X.-Z, et al., Efficacy of detoxification of deoxynivalenol-contaminated corn by *Bacillus* sp. LS100 in reducing the adverse effects of the mycotoxin on swine growth performance, Food Additives and Contaminants, vol. 28, No. 7, Jul. 2011, 894-901.

Yu, Hai, et al., Isolation of deoxynivalenol-transforming bacteria from the chicken intestines using the approach of PCR-DGGE guided microbial selection, BMC Microbiology 2010, 10:182.

Eriksen, G.S., et al., Toxicological evaluation of trichothecenes in animal feed, Animal Feed Science and Technology 114 (2004) 205-239.

He, P., et al., Micobial Transformation of Deoxynivalenol (Vomitoxin), Applied and Environmental Microbiology, Dec. 1992, p. 3857-3863.

Karlovsky, P., Biological Detoxification of Fungal Toxins and its Use in Plant Breeding, Feed and Food Production, Natural Toxins, Nat. Toxins 7: 1-23 (1999).

Swanson, S.P., et al., The Role of Intestinal Microflora in the Metabolism of Trichothecene Mycotoxins, Fd Chem. Toxic. vol. 26, No. 10, pp. 823-829, 1988.

Trenholm, H.L., et al., Two Physical Methods for the Decontamination of Four Cereals Contaminated with Deoxynivalenol and Zearalenone, J. Agric. Food Chem. 1991, 39, 356-360.

Young, J.C., et al., Degradation of trichothecene mycotoxins by chicken intestinal microbes, Food and Chemical Toxicology 45 (2007) 136-143.

* cited by examiner

Vomitoxin
4-deoxynivalenol (DON)

DOM-1

Toxic

Much Less Toxic

BACTERIAL ISOLATE AND METHODS FOR DETOXIFICATION OF TRICHOTHECENE MYCOTOXINS

RELATED APPLICATION

This application is the U.S. national phase, pursuant to 35 U.S.C. §371, of PCT international application Ser. No. PCT/CA2008/001402, filed Jul. 31, 2008, designating the United States and published in English on Feb. 5, 2009 as publication WO 2009/015478 A1, which claims priority to U.S. provisional application Ser. No. 60/953,301, filed Aug. 1, 2007. The entire contents of the aforementioned patent applications are incorporated herein by this reference.

FIELD OF INVENTION

The present invention relates to detoxification microorganisms. More specifically, the present invention relates to bacterial isolates and methods for detoxifying mycotoxins.

BACKGROUND OF THE INVENTION

Approximately 25% of the world's food crops are contaminated every year with mycotoxins, creating an ongoing, serious threat to human health and food and livestock industries. Control of mycotoxins is a global challenge due to their high toxicity to animals and humans and their widespread occurrence in agricultural commodities.

Trichothecene mycotoxins represent one of the most important mycotoxin classes that comprising naturally occurring metabolites produced primarily by *Fusarium* but also other species of fungi (*Stachybotrys, Myrothecium*, and *Trichothecium*) on a variety of cereal grains. The mycotoxins are known to be associated with several diseases in animals and humans (Ueno, 1983; Miller and Trenholm, 1994; Pittet, 1998; D'Mello et al., 1999; Placinta et al., 1999; DeVries et al., 2002; Conkova et al., 2003; Sudakin, 2003; Eriksen and Pettersson, 2004; Desjardins, 2006). Deoxynivalenol (DON or vomitoxin) is a specific trichothecene mycotoxin which is frequently encountered in human foods. DON is associated primarily with *Fusarium graminearum* (*Gibberella zeae*) and *F. culmorum*, fungal pathogens causing head blight (scab) of small-grain cereals and ear rot of maize.

Annually, about 10 million hectares wheat and 1.4 million hectares maize are seeded in Canada. Accordingly, control of mycotoxin contamination has been one of the major challenges facing the cereal industry. A survey conducted in Eastern Canada during 1991 to 1998 found that maize had the highest incidence of DON contaminated samples (0.1 mg/kg and over), which was 90%, followed by wheat, 82%, and barley 73%. In 2003, DON was detected in 63% of samples obtained from cereal-based infant foods from the Canadian retail market. Many outbreaks of acute human diseases have been attributed to consumption of *Fusarium*-contaminated grains and, more recently, to the presence of DON at reported concentrations of 3-93 mg/kg in grain for human consumption (Canady et al., 2001).

Mycotoxin contamination of feed ingredients also has been a serious threat to livestock industry, particularly swine production. It is well known that consumption of DON-contaminated feed can cause loss of appetite, vomiting, lesions of the intestinal tract and immunosuppression in animals (Eriksen and Pettersson 2004). Weight gain of pigs can be reduced by 5 to 10% with DON levels between 1 and 2 parts per million (ppm) and may be reduced by 50% if toxin levels in consumed feed are in the order of about 5 to 10 ppm (Purdue University; OMAFRA).

The current practice to reduce or contain mycotoxin contamination is focused mainly on the prevention of contaminated grain materials from entering the food chain through regulation, detection and compliance. However, since efficient prevention of mycotoxin contamination is not always feasible or practical, various physical, chemical and biological methods have been studied for use in decontamination of grains containing trichothecenes. For example, cleaning methods, such as gravity and sieving separation, dehulling and washing procedures can reduce the concentration of DON in wheat and maize (Trenholm et al., 1992). Thermal treatments by microwave or convection (Young, 1986) also may be used. Chemical detoxification by using oxidants such as ozone and sodium bisulfite (McKenzie, et al., 1997; Young, et al. 1986), reductants such as ascorbic acid (Swanson, et al., 1984) and alkali such as sodium hydroxide (Young et al., 1986) have been investigated. However, such treatments are often expensive, time intensive, lack efficiency, or produce deleterious side effects on the food products. Further, these methods often are not amenable to large volumes of food products and are generally considered undesirable by food/feed industries and/or consumers.

A variety of approaches have been used to reduce mycotoxin effects on livestock industries. The use of adsorbents as feed additives is common. Such adsorbents may include alfalfa fibre, hydrated sodium calcium aluminosilicate (HSCAS), bentonite, special types of clay, etc. The use of grains with no or low mycotoxin contamination to dilute mycotoxin level in feed is another common approach. Unfortunately, the use of adsorbents in feeds to remove mycotoxins is not only relatively expensive, but also specific to particular mycotoxins. Some of the most popularly used adsorbents, such as hydrated sodium calcium aluminosilicate (HSCAS) and the like, are not effective against DON. Further, the dilution method to reduce mycotoxin contamination by mixing contaminated ingredients with high quality grains is difficult to implement because the degree of contamination is often not known and thus there are questions about the extent of dilution needed to reach contamination levels which would be considered acceptable. Some European countries have already banned the use of this procedure.

Despite a plethora of information regarding the biochemistry, toxicity, and modes of action of mycotoxins, there still remain no viable solutions for either pre- or post-harvest control/eradication of these toxins (Cardwell et al., 2001). In developed countries, substantial costs are incurred through testing, compliance and research to prevent entrance of mycotoxins into the food chain. In the United States these costs are estimated to be about US $500 million to $1.5 billion per year (CAST, 1989). In Canada, losses of $100 million were accrued in 1996 following a *Fusarium* epidemic in Ontario (Schaafsma, 2002).

Today, the livestock feed industry is facing an even greater challenge due to the increased incidence of *Fusarium* ear rot of corn and the competition for corn from the emerging biofuel industry. One way in which both the biofuel industry and the livestock industry have been able to make synergistic use of the limited amount of corn available, is for the livestock industry to use the by-products created from the biofuel industry as a protein source to feed animals. However, ethanol fermentation does not destroy mycotoxins, such as DON, but, in fact, concentrates the levels to be 2 to 3 times higher than the starting material, which poses a serious risk to the livestock fed these by-products.

There is a need in the art for novel products and methods for mycotoxin control and/or decontamination. Further, there is a need in the art for specific, efficient and environmentally sound ways for decontamination/detoxification of mycotoxins.

SUMMARY OF THE INVENTION

The present invention relates to detoxification microorganisms. More specifically, the present invention relates to bacterial isolates and methods for detoxifying mycotoxins.

According to the present invention there is provided a bacterial isolate defined by accession number 180507-1 filed with the International Depository Authority of Canada.

Also provided by the present invention is a composition comprising bacteria as defined above.

The present invention also contemplates a composition as defined above, wherein the composition comprises a carrier.

Also provided by the present invention is a composition as defined above, wherein the carrier is a medium that promotes growth and/or survival of bacteria. Preferably, the medium is a cell culture medium.

Also provided by the present invention is a composition as defined above, wherein the carrier is a food or food product contaminated or susceptible to contamination by trichothecene mycotoxins or organisms that produce trichothecene mycotoxins.

Also provided by the present invention is a composition as defined above, wherein the carrier is a crop or harvested crop contaminated or susceptible to contamination by trichothecene mycotoxins or organisms that produce trichothecene mycotoxins.

The present invention also contemplates a composition as defined above wherein the trichothecene mycotoxins comprise deoxyinvalenol (vomitoxin).

Also provided by the present invention is a method of preventing or reducing mycotoxin contamination in a food or food product by treating the food or food product with bacteria as defined above.

Also provided by the present invention is a method of preventing or reducing mycotoxin contamination in a crop or harvested crop by treating the crop or harvested crop with bacteria as defined above.

The present invention also contemplates a method as defined above, wherein the mycotoxin contamination comprises trichothecene mycotoxins, preferably deoxynivalenol (vomitoxin).

The present invention also contemplates a method as defined above, wherein the efficiency of transformation from DON to DOM is defined by:

$$DON \text{ to } DOM(\%) = -783.228 + 165.854c + 24.895d - 0.049DON - 7.794c^2 - 2.214cd - 0.185d^2 + 0.000556cDON + 0.0000692dDON + 0.000109DON^2,$$

wherein c is the concentration of bacterial isolate 180507-1 (IDAC); d is the length of incubation; and DON is the concentration of DON.

The present invention also contemplates use of the composition as defined above for treatment of mycotoxin contaminated food or food products.

Also provided by the present invention is use of the composition as defined above for treatment of mycotoxin contaminated crops or harvested crops.

The present invention also provides a food additive comprising the bacteria as defined above.

The present invention also provides a kit comprising bacteria as defined above and one or more of the following:

a) one or more carriers for holding, suspending, diluting, adhering, enveloping, culturing, growing, freezing/cryopreserving or producing active metabolites from the bacteria;

b) one or more devices for combining or formulating the bacteria with the one or more carriers of a);

c) one or more devices for treating a food or food product with the bacteria or a composition comprising the bacteria, and;

d) instructions for growing the bacteria, formulating the bacteria with the one or more carriers, using one or more devices for treating a food or food product, or a combination thereof.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
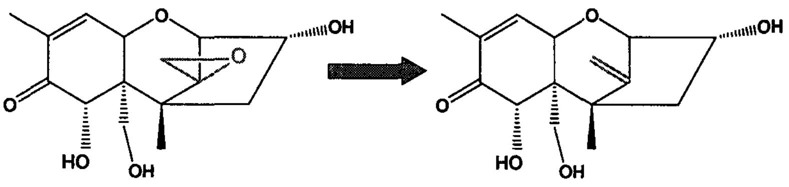
FIG. 1 shows the structures and conversion of vomitoxin (4-deoxynivenol (DON) to a less toxic compound de-epoxy-vomitoxin (DOM-1 or DOM).

The following description is of a preferred embodiment.

Provided herein is the isolation and identification of microorganisms capable of detoxifying trichothecene mycotoxins to less toxic products, for example, but not limited to, detoxification of vomitoxin (4-deoxynivalenol or DON) to the less toxic product de-epoxy-vomitoxin (DOM or DOM-1). Detoxification of trichothecene mycotoxins such as vomitoxin may occur by one or more routes, for example, but not limited to de-epoxidation. The epoxide ring of trichothecenes is responsible for their toxicity and de-epoxidation can result in a significant loss of toxicity (Eriksen and Pettersson 2004).

According to the present invention there is provided a bacterial isolate defined by accession number 180507-1 filed with the International Depository Authority of Canada (IDAC), 1015 Arlington Street, Winnipeg, Canada R3E 3R2 on May 18, 2007. Bacteria from the isolate exhibit mycotoxin detoxifying activity, for example, but not limited to vomitoxin (DON) detoxification activity.

The present invention also provides a composition comprising bacteria as defined by IDAC accession number 180507-1 and a carrier. By the term "carrier" it is meant a liquid, solid, liquid-solid or semi-solid substrate or medium for holding/retaining, suspending, diluting, adhering, enveloping, culturing, growing, proliferating, freezing/cryopreserving or any combination thereof, the bacteria as defined above. For example, but not to be considered limiting in any manner, the carrier may comprise a culture medium, such as, without limitation, L10 or another suitable medium as would be known in the art. Other carriers including culture media and the like as would be evident to a person of skill in the art are also meant to be encompassed by the term "carrier" as used herein. In a preferred embodiment, the carrier does not substantially affect the detoxification ability of the bacteria in association therewith.

It is also contemplated that the carrier also may comprise a food, food product or a combination of food or food products. By the phrase "food or food products" it is meant any food/feed or combination of foods/feeds, either in natural, harvested or processed form for human and/or animal consumption. The phrase "food or food product" also includes a by-product from a process which can later be used as a primary source of food or a product added to a food or diet. Any food or food product that comprises trichothecene mycotoxins, that is capable of being contaminated by trichothecene mycotoxins or that is susceptible to infection by microorganisms producing trichothecene mycotoxins are specifically included as food or food products herein. Representative examples of foods or food products include without limitation cereals for example, but not limited to corn, barley, rice, wheat, oats, sorghum, rye or mixtures thereof.

Accordingly, there is provided a composition comprising bacteria as defined by accession number 180507-1 and a carrier, wherein the carrier is food or food product, for example a human or animal food or feed product. In a preferred embodiment the food or food product is contaminated or susceptible to contamination by deoxynivalenol (vomitoxin) or microorganisms that are capable of producing deoxynivalenol. Similarly, there is contemplated a food or food product that comprises bacteria defined by accession number 180507-1 or that is treated to comprise the bacteria as defined by accession number 180507-1.

It is also contemplated that the carrier may also comprise a crop or harvested crop, which may or may not include plants that act as food for humans or animals. For example, plants grown for economic purposes, including for use in textiles, are encompassed by the phrase "crop or harvested crop". By definition, the phrase "crop or harvested crop" the plant can be either in the ground growing or has been harvested. Any crop or harvested crop that comprises trichothecene mycotoxins, that is capable of being contaminated by trichothecene mycotoxins or that is susceptible to infection by microorganisms producing trichothecene mycotoxins are specifically included as crop or harvested crop herein. Representative examples of crops or harvested crops include without limitation tobacco, switchgrass, jute, cotton and hemp. Accordingly, there is provided a composition comprising bacteria as defined by accession number 180507-1 and a carrier, wherein the carrier is crop or harvested crop. In a preferred embodiment the crop or harvested crop is contaminated or susceptible to contamination by deoxynivalenol (vomitoxin) or microorganisms that are capable of producing deoxynivalenol. Similarly, there is contemplated a crop or harvested crop that comprises bacteria defined by accession number 180507-1 or that is treated to comprise the bacteria as defined by accession number 180507-1.

The present invention also provides a method of reducing mycotoxin contamination in a food, food product, crop or harvested crop by treating the food, food product, crop or harvested crop with bacteria as defined by accession number 180507-1 or a composition comprising bacteria as defined by accession number 180507-1. In a preferred embodiment, the mycotoxins comprise trichothecene mycotoxins, more preferably deoxynivalenol (vomitoxin).

The present invention also provides a method of preventing mycotoxin contamination in a food, food product, crop or harvested crop by treating the food, food product, crop or harvested crop with bacteria as defined by accession number 180507-1 or a composition comprising bacteria as defined by accession number 180507-1. In a preferred embodiment, the mycotoxins comprise trichothecene mycotoxins, more preferably deoxynivalenol (vomitoxin).

Also contemplated by the present invention is a kit comprising bacteria as defined by accession number 180207-1 and one or more of the following:

a) one or more carriers;

b) one or more devices for combining or formulating the bacteria with the one or more carriers of a);

c) one or more devices for treating a food or food product with the bacteria or a composition comprising the bacteria as defined above, and;

d) instructions for growing the bacteria, formulating the bacteria with the one or more carriers, using one or more devices for treating a food or food product, or a combination thereof.

It is to be understood that the bacteria as defined in above may be combined with the one or more carriers as defined in a) or the two may be separate. Also possible is a kit that comprises bacteria or metabolites thereform, bacteria and carrier, and carrier as three or more separate components.

The present invention will be further illustrated in the following examples.

EXAMPLES

Example 1

Detoxification of Deoxynivalenol with Bio-Transforming Microorganisms

Deoxynivalenol (DON) or vomitoxin can be transformed to a much (several hundred times) less toxic compound, de-epoxy vomitoxin (DOM-1 or DOM) by microorganisms (FIG. 1). The contents from the large intestine of chickens was able to detoxify vomitoxin by converting DON (either as a pure chemical or in contaminated grains) to DOM-1, while contents from other gut regions showed little or no activity. Table 1 shows the ability of different species of chicken to convert DON to DOM-1. The White Leghorn hens were much more efficient at converting DON to DOM-1 than were Isa Brown hens. The detoxification appeared to be biological since autoclaved large intestinal samples showed no activity of detoxification. Detoxification of vomitoxin in contaminated grains was also examined at different incubation temperatures. Although the conversion rate was slightly higher at 30° C., incubation at both 30° C. and 37° C. was able to convert DON to DOM-1 in contaminated wheat and corn (Table 2).

TABLE 1

| Effect of individual hen* | | |
|---|---|---|
| Breed | Hen | Conversion Rate (%) |
| Isa Brown | 1 | 20 |
| | 2 | 18 |
| White Leghorn | 1 | 84 |
| | 2 | 51 |

*Incubation of the chicken large intestinal contents with DON (a pure chemical) at 30° C. for 96 hr in an anaerobic medium.

TABLE 2

| Effects of the DON source and incubation temperature* | | |
|---|---|---|
| | Conversion Rate (%) | |
| Temperature | Wheat | Corn |
| 30° C. | 43 | 36 |
| 37° C. | 33 | 31 |

*Incubation of the chicken large intestinal contents with DON (in contaminated grains) in an anaerobic medium for 96 hr.

This data suggests that chicken gut comprises microbes that can detoxify vomitoxin. Further, different breeds of hens show different capacities for detoxification of vomitoxin.

Example 2

Detoxification of DON with Bio-Transforming Microorganisms

Digesta were collected from crop, small intestine and large intestine of Leghorn hens raised with feeds mixed with clean and contaminated wheat containing 0 or 10 ppm DON, respectively. The digesta were added either directly or after being autoclaved, to a medium containing purified DON. The resulting mixtures were incubated for 0, 24 and 72 hours and subcultured for six generations at 37° C. before being processed for chemical analysis. The extent of transformation of DON to DOM-1 was determined by using a Liquid chromatography-mass spectroscopy (LC-MS).

Figure 2:
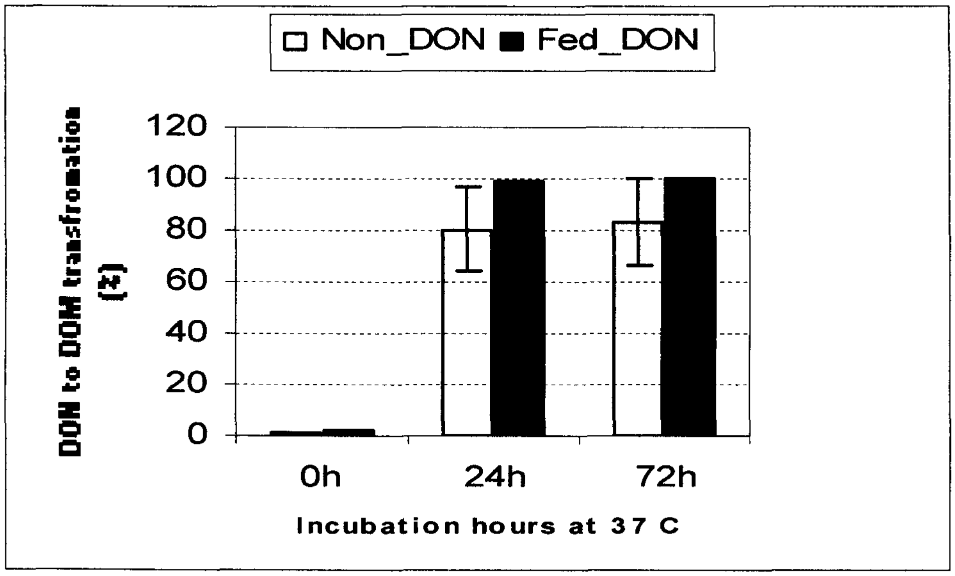
FIG. 2 shows results of tests confirming transformation of DON to DOM by large intestinal contents of chickens fed with and without vomitoxin.

Data presented in FIG. 2 showed that, compared to the non-DON control, digesta of the large intestine from chickens fed with contaminated wheat were more effective in transforming DON. Without wishing to be bound by theory or limiting in any manner, this may have resulted from increased population and/or improved efficacy of the active microorganisms in the chicken gut. The data also indicated that gut microorganisms acted rather quickly and in the assay conducted, could transform all DON to DOM within 24 hours.

Figure 3:
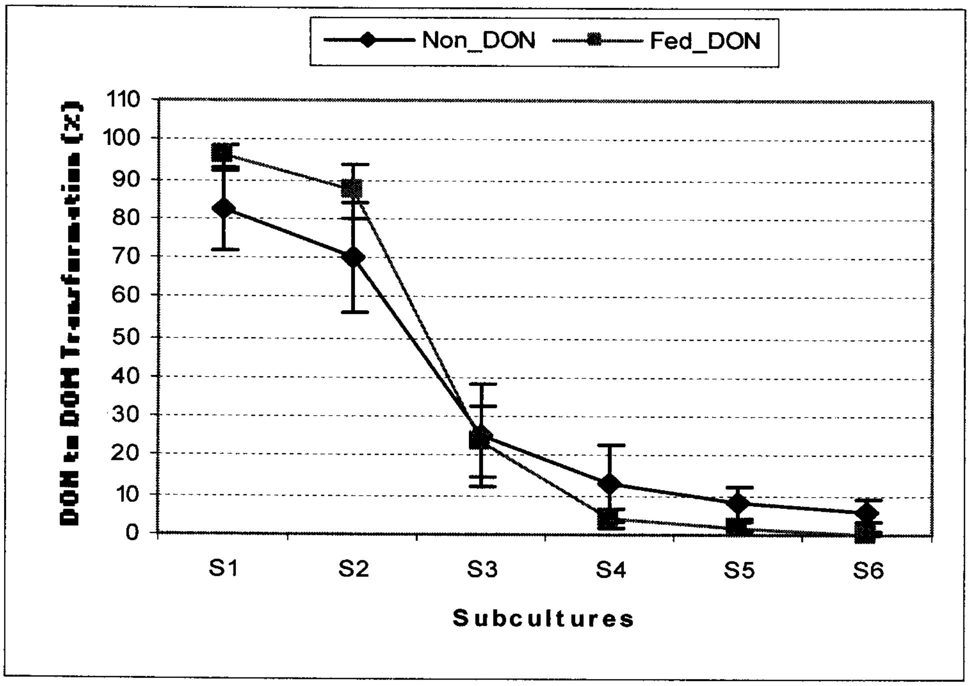
FIG. 3 shows results of transformation of DON to DOM by various subcultures of large intestinal contents of chickens fed with and without vomitoxin.

When digesta of large intestine were cultured in an artificial medium, the effectiveness of DON transformation was still high after the 2nd subculture, but significantly declined at the third subculture (FIG. 3).

Figure 4:
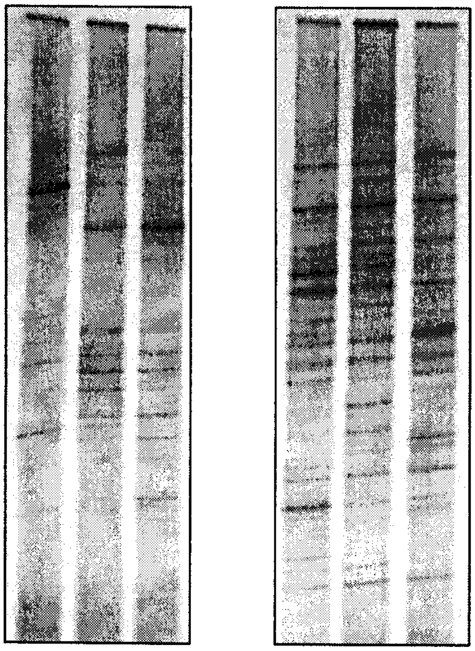
FIG. 4 shows DNA fingerprints of microorganisms from the small intestine (A) and large intestine (B) of Leghorn hens. Each band within a column represents a microorganism species. The results indicate that microflora of the Leghorn small intestine is much simpler than that of the large intestine.
Figure 5:
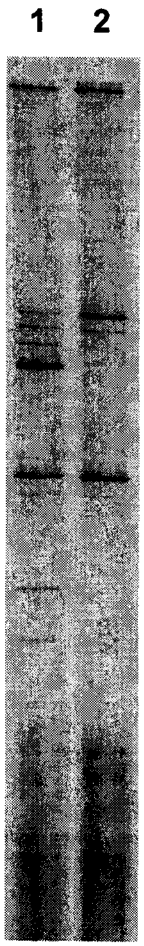
FIG. 5 shows a DNA fingerprint of microorganisms from chicken small intestinal contents. Each band represents a microorganism species. The microbial population was significantly simplified (2) by the use of antibiotics and selective media, as compared to the original culture (1).
Figure 6:
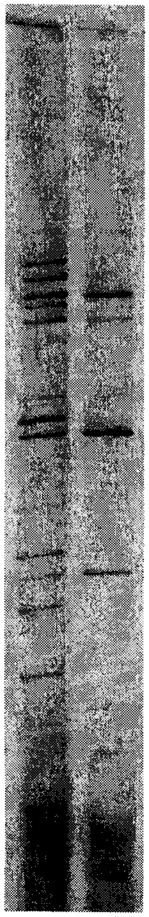
FIG. 6 shows a DNA fingerprint of microorganisms from chicken large intestinal contents. Each band represents a microorganism species. The microbial population was significantly simplified (2) by the use of antibiotics and selective media, as compared to the original culture (1).

Two out of four samples of small intestine showed substantial DON transformation activity although not all samples had activity. The results suggest that the microflora of the small intestine (A) is much less complex than that of the large intestine (B) (FIG. 4). Only one out of four samples from chicken crop had some DON detoxification activity.

Example 3

Identification/Isolation of bacterial isolate 18027-1 (IDAC)

Testing of a plurality of bacterial isolates, derived from various digestive regions of several chickens revealed that a variety of bacterial strains exist with differing abilities to detoxify trichothecene mycotoxins. Extensive screening allowed for the identification of a particular strain of bacteria with substantial trichothecene mycotoxin detoxifying activity. Characteristics of the bacterial isolate (termed bacterial isolate 180507-1 (IDAC) is described below.

Genomic DNA of the bacterial isolate 180507-1 (IDAC) was extracted with QIAGEN DNeasy Tissue Kit and 16S rRNA genes were amplified by PCR using eubacterial primers F8 (5'-AGAGTTTGATCCTGGCTCAG-3') (SEQ ID NO:1) and R1541 (5'-AAGGAGGTGATCCAAGCC-3') (SEQ ID NO:2). PCR products were directly sequenced using primer 16S1100r (5'-AGGGTTGCGCTCGTTG-3') (SEQ ID NO:3). Partial 16S rRNA sequences corresponding to *Escherichia coli* 16S rRNA gene bases 300 to 1050 were compared with the GenBank, EMBI, and DBJI nonredundant nucleotide databases using BLAST.

The resulting 16S rRNA gene (SEQ ID NO:4) from bacterial isolate 180507-1 (IDAC) had 96% sequence similarity to four separate strains from the *Bacillus* genus (Table 3).

TABLE 3

| Sequence similarity of 16S rRNA gene from bacterial isolate 180507-1 (IDAC) | | |
|---|---|---|
| | GenBank Accession # | Similarity (%) |
| *Bacillus senegalensis* strain RS6 | AF519466.1 | 96 |
| *Bacillus niacini* strain YM1C7 | EU221338.1 | 96 |
| *Bacillus novalis* strain LMG 21837 | AJ542512.1 | 96 |
| *Bacillus drentensis* strain WN575 | DQ275176.1 | 96 |

Bacterial isolate 180507-1 grows in an environment between 15° C. and 55° C. and pH of 4 to 10, preferably between 37° C. and 42° C. and a pH of 6 to 8. The environmental requirements for growth, in terms of temperature and pH, is similar to other species of the *Bacillus* genus. However, comparatively the colony size of bacterial isolate 180507-1 (IDAC) is smaller, less spreading and capable of anaerobic growth compared to other species from the genus.

As shown in Table 4, bacterial isolate 180507-1 (IDAC) is sensitive to vancomysin; cannot grow on MacConkey agar; does not release DNA when exposed to potassium hydroxide; and turns purple when Gram stained, which are all characteristic of a gram-positive bacteria.

TABLE 4

| Gram reactivity of bacterial isolate 180507-1 (IDAC) | | |
|---|---|---|
| Test | Reaction | Gram Reactivity |
| Gram stain | Purple | Positive |
| 3% KOH | No DNA release | Positive |
| Vancomysin (5 μg/disc) | Sensitive | Positive |
| Growth on MacConkey agar | No | Positive |

It was observed through microscopic examination that bacterial isolate 180507-1 (IDAC) is motile, has slightly curved, round ended rods, occurs singly, in pairs and occasionally in longer filaments. From a macroscopic examination following the growth on Tryptic Soy Agar (TSA), bacterial isolate 180507-1 (IDAC) colonies are slightly irregular in shape, raised in elevation, with undulated margins and have a rough grainy textured surface (Table 5). After one day on TSA, colonies were 2-2.5 mm in diameter and cream-coloured. This morphology is typical of a strain of the *Bacillus* genus.

The bacterial isolate 180507-1 (IDAC) was shown to have a catalase enzyme and was able to decompose 3% hydrogen peroxide into water and oxygen (Table 5). The presence of a catalase capable of decomposing 3% hydrogen is typical of *Bacillus*.

The fatty acid profile of bacterial isolate 180507-1 (IDAC) is unique when compared to the four strains that were shown to have similar 16S rRNA gene sequences, namely *B. subtilis, B. niacini, B. drentensis* and *B. novalis* (Table 5).

TABLE 5

| Summary of biochemical analysis | |
|---|---|
| Test | Result |
| Catalase | Positive |
| Morphology on TSA/BP | Typical *Bacillus* |
| 16S rRNA sequence | *Bacillus* |
| Fatty acid profile | Unique compared to 4 reference *Bacillus* strains |
| Fatty acid utilization | Unidentified |

Bacterial isolate 180507-1 (IDAC) profile indicates that it is a previously unidentified *Bacillus* gram-positive strain.

Consistency of isolate 180507-1 (IDAC): Isolate 180507-1 (IDAC) was sub-cultured 6 times or passages in L10 medium (Caldwell and Bryant, 1966) with 100 μg/ml DON, and gave 100% of DON to DOM transformation each time when tested under the assay conditions. After an additional 3 sub-culturing steps in medium without DON, the isolate still showed high activity in the assay and was capable of transforming DON to DOM at the 10th subculture. This indicates that the DON to DOM detoxification activity of isolate 180507-1 (IDAC) is stable. To examine stability of the bio-transformation activity, the isolate was sub-cultured six times in L10 medium with 100 ppm DON therein. At the end of each sub-culturing passage, DON or DOM was analyzed. Three hundred μl of the bacterium culture were added to 2700 μl of L10 medium plus DON, and incubated at 37° C. for 72 hours in an anaerobic atmosphere with 95% $CO_2$ and 5% $H_2$. This is defined as one sub-culture or one generation. To determine whether the activity is stable in the sub-culturing without DON in the medium, the isolate was sub-cultured 3 additional times in the medium without DON. At the tenth sub-culturing step, 100 ppm DON was added into the medium and DON or DOM was analyzed. DON was completely transformed into DOM at the tenth sub-culturing.

Initial concentration of isolate 180507-1 (IDAC): A culture of isolate 180507-1 (IDAC) was grown in L10 medium at 37° C. for 24 hours and diluted serially with the same medium into final concentrations from $10^1$-$10^8$ cells/ml and 100 μg/ml DON was added to each dilution. After 24-hour incubation at 37° C., samples were taken from each of the dilutions for analyzing de-epoxidation activity and for measuring cell concentrations. The results showed that under the conditions tested, isolate 180507-1 (IDAC) can completely transform DON into DOM within 24-hours when initial cell concentrations are equal to or greater than $10^5$ cells/ml.

Effects of DON concentrations on efficacy of isolate 180507-1 (IDAC): When the initial cell concentration was $10^8$ cells/ml in L10 medium, 100%, 100% and 48% of DON was transformed into DOM after 12-hour incubation at 37° C., as the initial concentrations of DON were 100, 200 and 1000 μg/ml, respectively. However, 100% transformation of DON into DOM was achieved in the treatment with 1000 μg/ml in a 24-hour incubation period.

Efficiency of isolate 180507-1 (IDAC): Effects of initial cell concentration, duration of incubation, and DON concentration on efficacy of the bacterial isolate in transforming DON to DOM were carefully assessed and adequately described by a polynomial regression model:

DON to DOM (%)=−783.228+165.854c+24.895d−0.049DON−7.794$c^2$−2.214cd−0.185$d^2$+0.000556*c*DON+0.0000692*d*DON+0.000109*$DON^2$ ($R^2$=0.991; where c is initial cell concentration, d is duration of incubation, DON is the concentration of DON). The minimum requirement of initial cell concentrations and duration of incubation for a complete transformation of DON to DOM with 200 μg/ml DON initial concentration has been predicted based on the regression equation (see Table 6).

TABLE 6

| Conversion of DON (200 μg/ml) to DOM (%) Initial Cell Concentration (Log cfu/ml) | | | | | |
|---|---|---|---|---|---|
| Incubation Period (h) | 4 | 5 | 6 | 7 | 8 |
| 12 | | | | | 100 |
| 18 | | | | 100 | |
| 24 | | | 100 | | |
| 32 | | 100 | | | |
| 40 | 98.9 | | | | |

The results provided herein show that bacterial isolate 180507-1 (IDAC) derived from the chicken gut possesses the ability to transform trichothecene mycotoxins, for example, but not limited to vomitoxin to its de-epoxided form, resulting in significant reduction in toxicity.

Degradation of trichothecenes other than DON: Degradation of trichothecenes other than DON was performed as described previously in Young, J. C., Zhou, T., Yu, H., Zhu, H., Gong, J., Degradation of Trichothecene Mycotoxins by Chicken Intestinal Microbes, Food and Chemical Toxicology (2007) 45: 136-143. The selected isolate also degraded eleven trichothecene mycotoxins, including 3-acetyldeoxynivalenol, 15-acetyldeoxynivalenol, 4-diacetoxyscirpenol, fusarenon X, HT-2 toxin, 15-monoacetoxyscirpenol, neosolaniol, nivalenol, T2 toxin, T-2 triol and verrucarol. Without wishing to be bound by theory or limiting in any manner, the resulting degradation occurred either by deepoxidation and/or deacylation. The route depends upon the presence and position of acyl functionalities and other molecular structures of the mycotoxins (Young et al., 2007).

Example 4

Biological Effects of DON-Contaminated Corn Consumption in Swine

Seven pigs were assigned to the control group and seven pigs were assigned to the test group. Both groups were subjected to a 9-day pre-trial diet which consisted of a base diet containing 68.38% corn+wheat+barley, 27% soy meal and 4.62% mineral and vitamin supplement. The test animals were then placed on a moldy corn diet for 9 days. The moldy corn was pretreated by autoclaving and assayed for DON concentration prior to addition to the base diet. Four kilograms of moldy corn having an average DON concentration of 124 ppm were mixed with 105 kg of base diet to give a 5 ppm DON diet. For the same period of time, control pigs were fed a basal diet that was supplemented with clean (no detectable amount of DON) corn in the same amount as the moldy corn (4 kg to 105 kg base diet). Following the trail period, both groups were once again placed on the basal diet for a further 11 days.

As shown in Table 7, swine that were fed the moldy corn diet for the trial period showed a significant decrease in average daily feed intake (ADFI), average daily weight gain (ADG) and feed efficiency (gain:feed) compared to those swine on the clean corn diet. Once the moldy corn was removed from the test animals' diet, they quickly began to consume food in amounts similar to the control animals. Similarly, their average daily weight gain and feeding efficiency rebounded to levels observed in the control animals.

TABLE 7

Growth performance of starter pigs fed clean and DON-contaminated diets

| | Control | DON-contaminated diet (5 ppm) | Statistical significance (P) |
|---|---|---|---|
| Pre-trial (day 0-9) | | | |
| ADG (g/d) | 775 | 799 | 0.8157 |
| ADFI (g/d) | 1,246 | 1,255 | 0.7097 |
| Gain:feed | 0.62 | 0.64 | 0.9198 |
| Toxin period (day 9-18) | | | |
| ADG (g/d) | 882 | 458 | <0.0001 |
| ADFI (g/d) | 1,337 | 943 | 0.0001 |
| Gain:feed | 0.66 | 0.47 | 0.0081 |
| Post-toxin (day 18-29) | | | |
| ADG (g/d) | 916 | 1,056 | 0.2427 |
| ADFI (g/d) | 1,648 | 1,680 | 0.9870 |
| Gain:feed | 0.55 | 0.63 | 0.1647 |

To determine whether the DON-contaminated diet caused changes in the blood profile of the animals, blood samples were taken from the retro-orbital sinus daily during the toxin or test period. Serum samples were tested for total protein, albumin, globulin, glucose, betahydroxybutane, haptoglobin, urea, cholesterol, creatinine, bilirubin, calcium, phosphorus, magnesium, sodium, potassium chloride, and activities of alkaline phosphatase, glutamate dehydrogenase (GLDH), aspartate aminotransferase, gamma glutamyltransferase (GGT), and creatine kinase.

The haematological and biochemical values were within normal limits, even when differences occurred among groups. As shown in Table 8, statistically significant differences were measured between the control and the DON-contaminated fed group with respect to the amount of urea, GLDH, total bilirubin and conjugated bilirubin in the blood.

TABLE 8

Serum metabolites of starter pigs fed clean and DON-contaminated diets

| | Control | DON-contaminated diet (5 ppm) | Statistical significance (P) |
|---|---|---|---|
| Calcium mmol/L | 2.93 | 3.04 | 0.9667 |
| Phosphorus mmol/L | 3.18 | 2.81 | 0.0876 |
| Magnesium mmol/L | 0.87 | 0.88 | 0.9119 |
| Sodium mmol/L | 142.67 | 141.00 | 0.6594 |
| Potassium mmol/L | 5.18 | 5.10 | 0.5771 |
| Chloride mmol/L | 102.50 | 101.63 | 0.7030 |
| Na:K Ratio mmol/L | 27.50 | 28.00 | 0.5646 |
| Total protein g/L | 55.00 | 53.75 | 0.3543 |

TABLE 8-continued

Serum metabolites of starter pigs fed clean and DON-contaminated diets

| | Control | DON-contaminated diet (5 ppm) | Statistical significance (P) |
|---|---|---|---|
| Haptoglobin g/L | 0.25 | 0.17 | 0.6214 |
| Albumin g/L | 41.83 | 43.38 | 0.9469 |
| Globulin g/L | 13.17 | 10.38 | 0.4102 |
| A:G Ratio | 3.41 | 4.36 | 0.2520 |
| Urea mmol/L | 2.20 | 2.68 | 0.0270* |
| Creatinine mmol/L | 68.50 | 80.50 | 0.1333 |
| Glucose mmol/L | 6.52 | 6.46 | 0.8001 |
| Cholesterol mmol/L | 2.07 | 2.07 | 0.9594 |
| Alkaline Phosphatase U/L | 246.17 | 249.63 | 0.3497 |
| Gamma-GT U/L | 22.67 | 28.63 | 0.2876 |
| AST U/L | 30.67 | 40.25 | 0.6071 |
| CK U/L | 3,843 | 7,722 | 0.8217 |
| GLDH U/L | 0.83 | 0.50 | 0.0124* |
| Total Bilirubin mmol/L | 0.50 | 0.25 | 0.0307* |
| Conjugated Bilirubin mmol/L | 0.33 | 0.00 | 0.0151* |
| Free Bilirubin mmol/L | 0.17 | 0.25 | 0.3742 |
| Calculated Osmo mmol/L | 283.67 | 281.00 | 0.7779 |

significantly different $P < 0.05$

Example 5

The Growth Effects of a Diet Containing DON-contaminated Corn Treated with Bacterial Isolate 180507-1 (IDAC) in Swine Moldy corn stock used in Example 4 was treated with bacterial isolate 180507-1 (IDAC) prior to introduction to the basal swine diet noted hereinabove. In particular, 100 grams of autoclaved (121° C., 15 min) moldy corn per 250 mL bottle was mixed with 50 mL anaerobic culture medium, 175 ml $Na_2CO_3.H_2O$ (0.4% to bring the pH to 10.6) and 25 mL 180507-1 (IDAC) cell culture ($4\times10^9$ CFU $ml^{-1}$) and incubated in an anaerobic chamber for 72 hours at 37° C. Similarly, clean corn was treated in the same manner to control for any biological effects brought on by bacterial isolate 180507-1 (IDAC).

The treatment schedule was identical to the schedule described in Example 4. In addition to the control group and the DON-contaminated diet group described in Example 4, a group of seven swine were fed the bacterial isolate 180507-1 treated moldy corn diet during the toxin period and another seven swine were fed the bacterial isolate 180507-1 clean corn diet during the same period.

As shown in Table 9, the average daily feed intake (ADFI), average daily weight gain (ADG) and feed efficiency (gain: feed) of pigs fed the bacterial isolate 180507-1 treated moldy corn diet were significantly different from those animals fed the DON-contaminated feed.

Swine fed clean corn and bacterial isolate 180507-1 clean corn during the toxin period had similar feed consumption, weight gain, and feed efficiency, suggesting that the bacterial isolate 180507-1 did not yield any compounds toxic to the pig or affected palatability of the feed.

TABLE 9

Growth performance of starter pigs fed non-treated and bacterial isolate 180507-1 treated clean and DON-contaminated diets

| | A | B | C | D | Statistical difference (P) A vs B | B vs C | B vs D |
|---|---|---|---|---|---|---|---|
| Pre-trial (day 0-9) | | | | | | | |
| ADG (g/d) | 775 | 799 | 793 | 796 | 0.8157 | 0.8827 | 0.5613 |
| ADFI (g/d) | 1,246 | 1,255 | 1,244 | 1,207 | 0.7097 | 0.1998 | 0.7036 |
| Gain:feed | 0.62 | 0.64 | 0.64 | 0.66 | 0.9198 | 0.5188 | 0.7301 |
| Toxin period (day 9-18) | | | | | | | |
| ADG (g/d) | 882 | 458 | 835 | 835 | <0.0001 | 0.0008 | 0.0029 |
| ADFI (g/d) | 1,337 | 943 | 1,367 | 1,347 | 0.0001 | <0.0001 | 0.0033 |
| Gain:feed | 0.66 | 0.47 | 0.62 | 0.61 | 0.0081 | 0.0994 | 0.0404 |
| Post-toxin (day 18-29) | | | | | | | |
| ADG (g/d) | 916 | 1,056 | 890 | 899 | 0.2427 | 0.0490 | 0.1148 |
| ADFI (g/d) | 1,648 | 1,680 | 1,629 | 1,628 | 0.9870 | 0.4478 | 0.5000 |
| Gain:feed | 0.55 | 0.63 | 0.55 | 0.55 | 0.1647 | 0.0857 | 0.1786 |

The present invention has been described with regard to one or more embodiments. However, it will be apparent to persons skilled in the art that a number of variations and modifications can be made without departing from the scope of the invention as defined in the claims.

REFERENCES

Caldwell, D. R., and Bryant, M. P., 1966. Medium without rumen fluid for nonselective enumeration and isolation of rumen bacteria. Appl. Environ. Microbiol. 14: 794-801.

Canady, R. A., Coker, R. D., Egan, S. K., Kraska, R., Kuiper-Goodman, T., Olsen, M., Pestka, J., Resnik S., Sclatter, J. 2001. Deoxynivalenol. In: Safety evaluation of certain mycotoxins in food. WHO Food Additives Series 47, WHO, Geneva, pp. 419-556.

Cardwell, K. F., Desjardins, A., Henry, S. H., Munkvoild, G. Robens, J. 2001. Discussion, In:APSnet Mycotoxins: The cost of food security and food quality. http://www.apsnet.org/online/feature/mycotoxin CAST (Council for Agricultural Science and Technology). 1989. Mycotoxin: Economic and Health Risks. Task Force Report No. 116.

Conkova, E., Laciakova, A., Kovac, G., Seidel, H., 2003. Fusarial toxins and their role in animal diseases. Vet. J. 165, 214-220.

DeVries, J. W., Trucksess, M. W., Jackson, L. S., 2002. Mycotoxins and Food Safety: Proceedings of an American Chemical Society Symposium held in Washington, D.C., USA, on 21-23 Aug. 2000. Kluwer Academic Publishers, Dordrecht, Netherlands, p. 295.

Desjardins, A. E., 2006. *Fusarium* Mycotoxins—Chemistry, Genetics, and Biology. American Phytopathology Society, St. Paul, Minn., USA.

D'Mello, J. P. F., Placinta, C. M., Macdonald, A. M. C., 1999. *Fusarium* mycotoxins: a review of global implications for animal health, welfare and productivity. Anim. Feed Sci. Technol. 80, 183-205.

Döll, S., Dänicke, S. Valenta, H. and Flachowsky, G. 2004. In vitro studies on the evaluation of mycotoxin detoxifying agents for their efficacy on deoxynivalenol and zearalenone. Archives of Animal Nutrition. 58: 311-324.

Eriksen, G. S, and Pettersson, H. 2004. Toxicological evaluation of trichothecenes in animal feed. Animal Feed Science and Technology 114: 205-239.

Gong, J., Zhou, T., Young, J. C., Cottrill, M., Yu, H., Zhu, H., de Lange, C. F. M., Du, W. and Cao, R. 2003. Gut microbes and mycotoxin: Can chicken gut microbes detoxify vomitoxin? Proceeding of the 22nd Annual Centralia Swine Research Update, Kirkton, Ontario. Pages 130-31.

He, P., Young, L. G., and Forsberg, C. 1992. Microbial transformation of deoxynivalenol (vomitoxin). Applied and Environmental Microbiology 58: 3857-3863.

Karlovsky, P. 1999. Biological detoxification of fungal toxins and its use in plant breeding, feed, and food production. Natural Toxins 7: 1-23.

McKenzie, K. S. 1997. Oxidative degradation and detoxification of mycotoxins using a novel source of ozone. Food and Chemical Toxicology 35: 807-820.

Miller, J. D., Young, J. C., Trenholm, H. L., 1983. *Fusarium* toxins in field corn. I. Time course of fungal growth and production of deoxynivalenol and other mycotoxins. Can. J. Botany 61, 3080-3087.

Pittet, A., 1998. Natural occurrence on mycotoxins in foods and feeds—an updated review. In: le Bars, J., Galtier, P., Burgat, V., Guerre, P. (Eds.), Revue de Medecine Veterinaire, pp. 479-492.

Placinta, C. M., D'Mello, J. P. F., Macdonald, A. M. C., 1999. A review of worldwide contamination of cereal grains and animal feed with *Fusarium* mycotoxins. Anim. Feed Sci. Technol. 78, 21-37.

Schaafsma, A. W. 2002. Economic changed imposed by mycotoxins in food grains: Case study of deoxynivalenol in winter wheat. Advances in Experimental Medicine and Biology 504: 271-276.

Sudakin, D. L., 2003. Trichothecenes in the environment: relevance to human health. Toxicol. Lett. 143, 97-107.

Swanson, S. P., Hagler, W. M., Rood, H. D. 1984. Destruction of deoxynivalenol (vomitoxin) with sodium bisulphate. Abstracts of the Annual Meeting, American Society for Microbiology. Abstract 019.

Swanson, S. P., Rood, H. D., Behrens, JR., J. C., and Sanders, P. E. 1987. Preparation and characterization of the deepoxy trichothecenes: deepoxy HT-2, deepoxy T-2 triol, deepoxy T-2 tetraol, deepoxy 15-monoacetoxyscirpenol and depeoxy scirpentriol. Applied Environmental Microbiology 53: 2821-2826.

Swanson, S. P., Helaszek, C., Buck, W. B., Rood Jr, H. D., Haschek, W. M. 1988. The role of intestinal microflora in the metabolism of trichothecene mycotoxins. Food and Chemical Toxicology 26: 823-829.

Trenholm, H. L., Charmley, L. L., Prelusky, D. B., Warner, R. M. 1991. Two physical methods for the decontamination of four cereals contaminated with deoxynivalenol and zearalenone. Journal of Agricultural and Food Chemistry 39: 356-360.

Trenholm, H. L., Charmley, L. L., Perlusky, D. B., Warner, R. M. 1992. Washing procedures using water or sodium carbonate solutions for the decontamination of three cereals contaminated with deoxynivalenol and zearalenone. Journal of Agricultural and Food.

Ueno, Y., 1983. Trichothecene-producing fungi. In: Ueno, Y. (Ed.), Developments in Food Science 4, Trichothecenes—Chemical, Biological and Toxicological Aspects. Elsevier, Amsterdam, Netherlands, p. 73.

Young, J. C., Zhou, T., Yu, H., Zhu, H., Gong, J., Degradation of Trichothecene Mycotoxins by Chicken Intestinal Microbes, Food and Chemical Toxicology (2007) 45: 136-143.

Zhou, T., Gong, J., Young, J. C., Yu, H., Zhu, H., Su, X. J., Li, X. Z., Yang, R. de Lange, C. F. M., Du, W. and Cao, R. 2005. Detoxification of vomitoxin with biotransforming microorganisms. Proceeding of the 23nd Annual Centralia Swine Research Update, Kirkton, Ontario. Feb. 6, 2005. Pages II 28-30.

Zhou, T., Gong, J., Young, J. C., Yu, H., Zhu, H., Cao, R., de Lange, C. F. M. and Du, W. 2005. Detoxification of vomitoxin by chicken gut microorganisms. An annual report to Ontario Pork, May, 2005.

What is claimed is:

1. A biologically pure culture of *Bacillus* IDAC 180507-1, which was isolated from chicken intestine and which is capable of detoxification of trichothene mycotoxins.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Eubacteria

<400> SEQUENCE: 1

agagtttgat cctggctcag                                                20


<210> SEQ ID NO 2
<211> LENGTH: 18
<212> TYPE: DNA
<213> ORGANISM: Eubacteria

<400> SEQUENCE: 2

aaggaggtga tccaagcc                                                  18


<210> SEQ ID NO 3
<211> LENGTH: 16
<212> TYPE: DNA
<213> ORGANISM: Eubacteria

<400> SEQUENCE: 3

agggttgcgc tcgttg                                                    16


<210> SEQ ID NO 4
<211> LENGTH: 1511
<212> TYPE: DNA
<213> ORGANISM: Bacillus

<400> SEQUENCE: 4

agagtttgat cctggctcag gacgaacgct ggcggcgtgc ctaatacatg caagtcgagc      60

gaatctttgg gagcttgctc ttttaagatt agcggcggac gggtgagtaa cacgtgggca     120

acctgcctgt aagacgggga taactccggg aaaccggggc taataccgga tgattcttct     180

ctgcacatgc agggaagcta aaagatggtt tacgctatcg cttacagatg ggcccgcggc     240

gcattagcta gttggtgagg taacggctca ccaaggcgac gatgcgtagc cgacctgaga     300

gggtgatcgg ccacactggg actgagacac ggcccagact cctacgggag gcagcagtag     360

ggaatcttcc acaatggacg aaagtctgat ggagcaacgc cgcgtgagcg atgaaggcct     420

tcgggtcgta aagctctgtt gttagggaag aacaagtact ggagtaactg ccggtacctt     480

gacggtacct aaccagaaag ccacggctaa ctacgtgcca gcagccgcgg taatacgtag     540
```

-continued

```
gtggcaagcg ttgtccggaa ttattgggcg taaagcgcgc gcaggcggtc ctttaagtct    600

gatgtgaaag cccccggctc aaccggggag ggtcattgga aactggagga cttgagtgca    660

gaagaggaaa gcggaattcc acgtgtagcg gtgaaatgcg tagagatgtg gaggaacacc    720

agtggcgaag gcggctttct ggtctgtaac tgacgctgag gcgcgaaagc gtggggagca    780

aacaggatta gataccctgg tagtccacgc cgtaaacgat gagtgctaag tgttaggggg    840

tttccgcccc ttagtgctgc agctaacgca ttaagcactc cgcctgggga gtacggccgc    900

aaggctgaaa ctcaaaggaa ttgacggggg cccgcacaag cggtggagca tgtggtttaa    960

ttcgaagcaa cgcgaagaac cttaccaggt cttgacatcc tctgacacac ctagagatag   1020

gtcttcccct tcgggggaaa gagtgacagg tggtgcatgg ttgtcgtcag ctcgtgtcgt   1080

gagatgttgg gttaagtccc gcaacgagcg caacccttga gattagttgc cagcattcgg   1140

ttgggcactc taatctgact gccggtgaca aaccggagga aggtggggat gacgtcaaat   1200

catcatgccc cttatgacct gggctacaca cgtgctacaa tggatggtac aaagggctgc   1260

gaaaccgcaa ggtgaagcca atcccataaa accattctca gttcggattg caggctgcaa   1320

ctcgcctgca tgaagccgga atcgctagta atcgcggatc agcatgccgc ggtgaatacg   1380

ttcccgggcc ttgtacacac cgcccgtcac accacgagag tttgtaacac ccgaagtcgg   1440

tggggtaacc gcaaggagcc agccgcctaa ggtgggacag atgattgggg tgaagtcgta   1500

acaaggtaac c                                                        1511
```